United States Patent [19]

Genese

[11] 4,036,232
[45] July 19, 1977

[54] ASPIRATION DEVICE

[75] Inventor: Joseph Nicholas Genese, Waukegan, Ill.

[73] Assignee: Abbott Laboratories, North Chicago, Ill.

[21] Appl. No.: 677,950

[22] Filed: Apr. 19, 1976

[51] Int. Cl.² ............................................. A61M 1/00
[52] U.S. Cl. .................................... 128/278; 128/2 F
[58] Field of Search ............................. 128/276–278, 128/2 F, 2 B, 2 R, 2 W, DIG. 5, 218 P, 218 M, 234, 237, 220

[56] References Cited

U.S. PATENT DOCUMENTS

| 3,835,835 | 9/1974 | Thompson et al. | 128/2 F |
|---|---|---|---|
| 3,885,549 | 5/1975 | Green | 128/276 |
| 3,939,835 | 2/1976 | Bridgeman | 128/276 |

*Primary Examiner*—William E. Kamm
*Assistant Examiner*—Henry S. Layton
*Attorney, Agent, or Firm*—Robert L. Niblack; Neil E. Hamilton

[57] ABSTRACT

An aspiration unit which will afford a uniform suction level for aspirating fluids from body cavities. The unit is composed of a double piston member, a first head of which is in sealing engagement with a syringe barrel and the second head which is oppositely disposed is contained in a telescoping member which is also receivable in the syringe barrel. Upon movement of the telescoping member outwardly from the syringe barrel, a vacuum will be created in the telescoping member as well as in that portion of the barrel member between the first piston member and the nozzle which is closed from atmosphere by means of a valve member. Upon insertion of a flexible tube into a body cavity and opening of the valve member, fluid will be aspirated into the syringe barrel by means of the partial vacuum created in the syringe barrel and in the telescoping member. A clamp means is provided to hold the telescoping member in the vacuum creating condition while the tubular member is inserted into a body cavity. The aspirating device is operable with one hand and is disposable.

11 Claims, 9 Drawing Figures

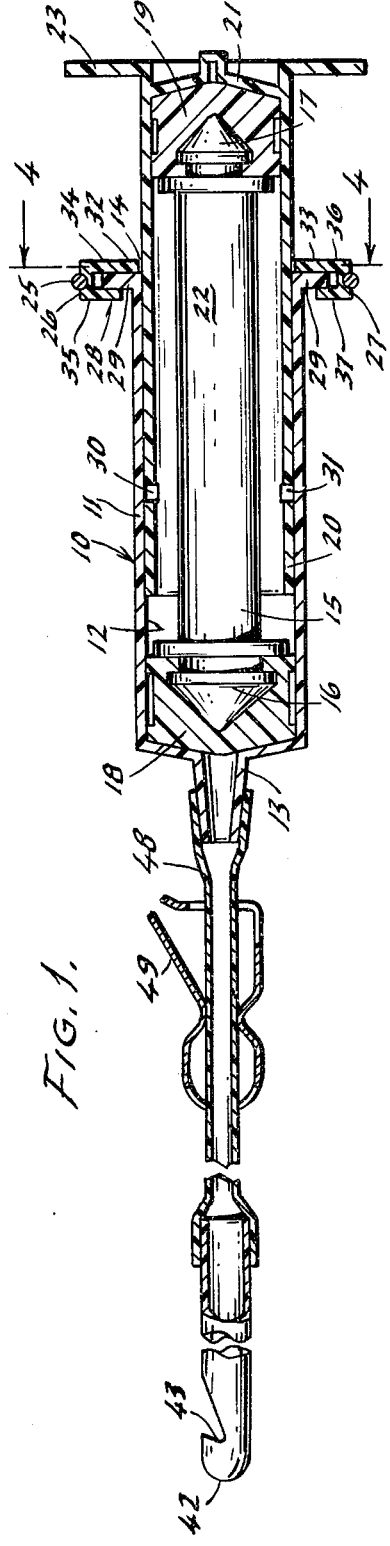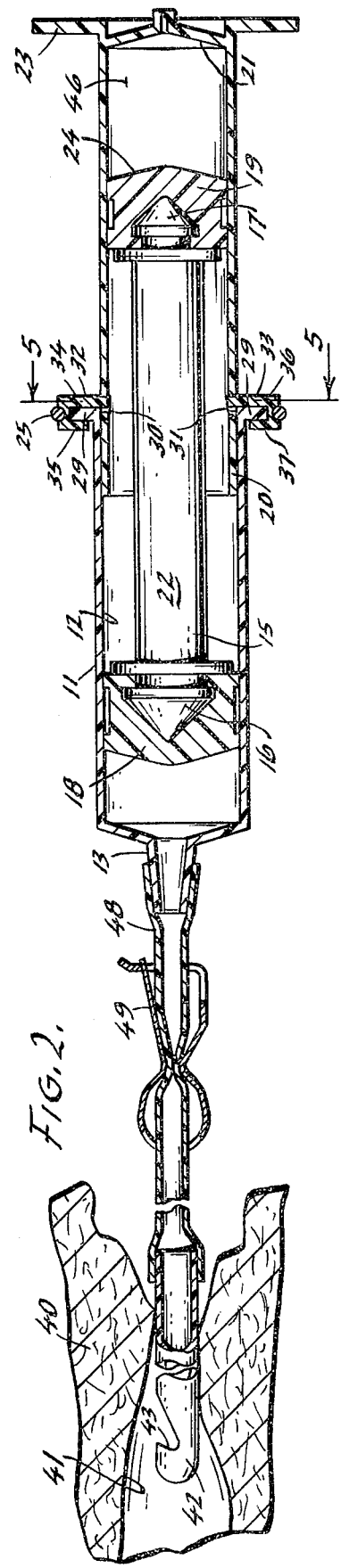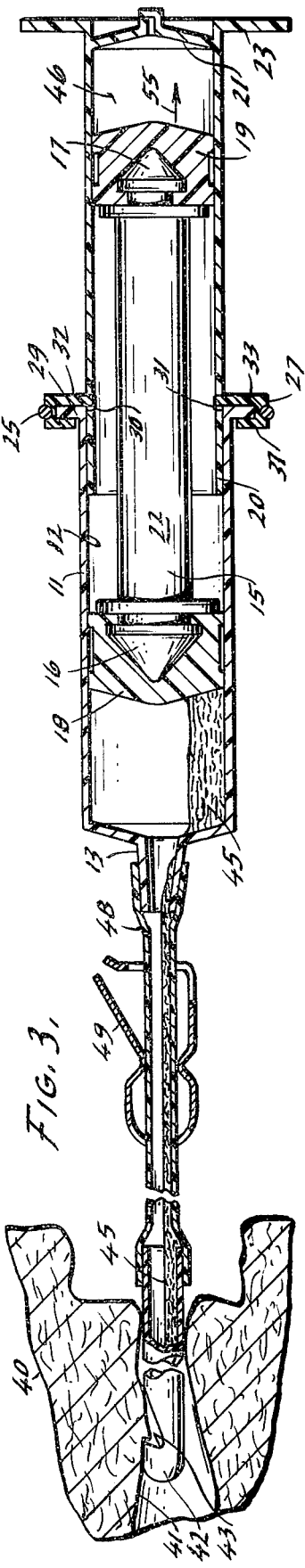

ASPIRATION DEVICE

BACKGROUND OF THE INVENTION

This invention relates to aspiration devices for body fluids. More particularly, it relates to a uniform suction device which, after preloading, is operable without external vacuum means by the opening of a valve member and will provide a uniform suction throughout the movement of the device.

Apparatus for collecting body fluids are described in U.S. Pat. No. 3,200,813 as well as in U.S. Pat. Nos. 3,382,856 and 3,706,305. All of these devices relate to either vacuumized syringe units or units which contain one or more compartments for the collection of fluids. In U. S. Pat. No. 2,646,042 a syringe-type aspirating unit is utilized in conjunction with a complex pressure equalizing apparatus as well as a syringe having concentric plungers.

None of the prior art teaches a double-headed piston member which is operable at one end in a syringe barrel and at the other end in a telescoping member receivable in the syringe barrel to effect a vacuum in the syringe which is releasable by mere manipulation of a valve member. All of the prior art units are either concerned with prevacuumized containers or collecting samples in a multiplicity of units which are pierced by a cannula member. None of the prior art devices teaches a simplified unit which can aspirate body fluids from relatively large body cavities by means of a uniform suction which can be created in the unit itself.

It is an advantage of the present invention to provide a novel aspirating device which will afford uniform suction over the length of the piston stroke effecting the vacuum. Other advantages are an aspirating unit which is capable of one-handed operation by means of the mere movement of a valve member; an aspirating unit which can aspirate relatively large volumes of fluid from relatively large body cavities; an aspirating unit which is completely disposable; an aspirating unit wherein the partial vacuum is created in the unit itself prior to its use and a uniform suction device which can be readily regulated by operation of a valve; a uniform aspirating device which can be interconnected to a large length of tubing for aspirating body fluids from a uterus.

SUMMARY OF THE INVENTION

The foregoing advantages are accomplished and the shortcomings of the prior art are overcome by the present apparatus which is composed of a double-headed piston member one end of which is received in the usual type of syringe barrel and the other receivable in a telescoping member which in turn is receivable in the barrel member. Holding means are provided in conjunction with the barrel member so as to hold the telescoping member in a fixed position when it is moved in a direction away from the nozzle portion of the barrel so as to effect a vacuum in the telescoping member when the nozzle portion is closed as by means of a length of tubing and a valve. In one embodiment, the holding means is a biased clamp member which has clamping portions to engage indentations in the telescoping member. In another embodiment the holding means is a projecting flange on the telescoping member and an inwardly projecting wall portion on the barrel which are interengaged by rotation of the telescoping member.

BRIEF DESCRIPTION OF DRAWINGS

A better understanding of the present apparatus will be afforded by reference to the drawing wherein:

FIG. 1 is a sectional view of one embodiment of the aspirating device of this invention attached to a length of flexible tubing having an aspirating tip.

FIG. 2 is a view similar to FIG. 1 showing the aspirating device in a loaded and clamped position and engaging inside a uterus.

FIG. 3 is a view similar to FIG. 2 except showing the unit in an aspirated condition in that the double-headed piston member has moved away from the nozzle thereby creating a vacuum in the syringe barrel and withdrawing fluid from the uterus.

DESCRIPTION OF ONE EMBODIMENT

Figure 4:
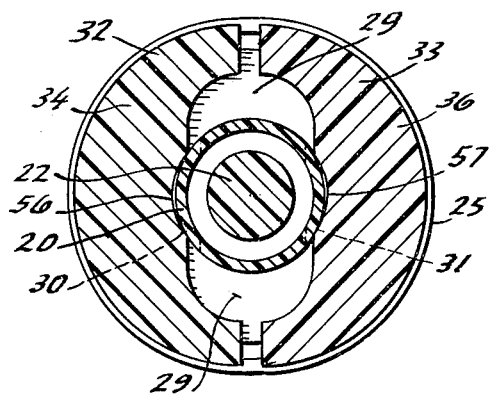
FIG. 4 is a view in vertical section taken through line 4—4 of FIG. 1 and with the unit rotated 90°.

Proceeding to a detailed description of the present invention, the aspiration device generally 10, is comprised of a barrel member 11 having an internal wall 12 with a nozzle portion 13. Opposite the nozzle portion 13 is an open end 14 for receiving a double-headed piston member 15. A first head of the piston member is indicated by the numeral 16 and the second by the numeral 17. Each of the piston heads 16 and 17 have sealing elements 18 and 19, respectively, with sealing element 18 in sealing engagement with the internal wall 12 of barrel 11. A telescoping member 20 is receivable in barrel member 11 and has an outside diameter slightly smaller than the inside diameter of barrel 11. Sealing element 19 on piston head 17 is in sealing engagement with the inside of telescoping member 20. Opposing indentations 30 and 31 are provided in telescoping member 20 with telescoping member 20 being closed by end portion 21 with the usual gripping flange 23 extending in opposite directions from the telescoping member. It will also be noted that piston member 15 has the opposing heads 16 and 17 interconnected by means of piston rod 22.

Extending outwardly from barrel 11 in opposing directions is a generally oval shaped flange 29 which receives and retains a biased clamp generally 28. Clamp 28 is composed of two semicircular sections 32 and 33 each of which have a generally cross-sectioned U-shaped configuration for surrounding the oval flange 29. Clamp section 32 has a rear portion 34 with arcuate segment 56 for riding on the outside of telescoping member 20 and a shorter front portion 35 which surrounds one segment of the oval flange. Correspondingly, clamp section 33 has a rear portion 36 with arcuate segment 57, and a front portion 37 for the same purpose. A biasing means 25 which is in the form of a rounded rubber band is held by an appropriate groove in each bridging segments 26 and 27 of clamp sections 32 and 33, respectively, between the front and rear portions 35, 37 and 34, 36. The biasing means will cause the longer rear portions 34 and 36 to contact the exterior wall surface of telescoping member 20 as shown in FIG. 1 and to be moved into slots 30 and 31 when they are oriented beneath the rear portions 34 and 36 as shown in FIG. 2 and as will be later explained in the operation. Extending from the nozzle portion 13 of aspirating device 10 is a length of flexible tubing 48 which ultimately is interconnected with a rigid tip member 42 having an opening 43. A valve clamp means 49 is connected to flexible tubing 48 for opening and closing it. As seen in FIGS. 2 and 3, tip 42 is in communication with a uterus 40 and the uterine cavity 41.

Figure 6:
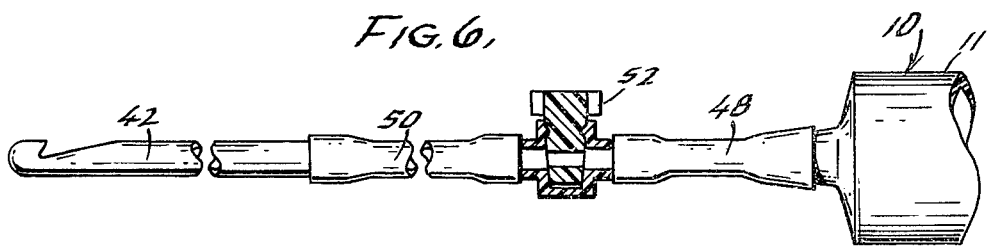
FIG. 6 is a partial view of the aspirating unit illustrating it in conjunction with a different valving member.

As shown in FIG. 6, in place of an on-off type clamp 49 is a common stop-cock type valve 52 which can be utilized in conjunction with aspirating device 10.

DESCRIPTION OF ANOTHER EMBODIMENT

Figure 7:
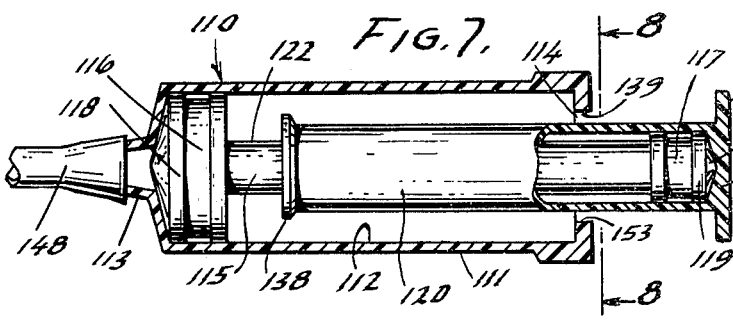
FIG. 7 is a view in vertical section of a modified embodiment of an aspirating device prior to its being moved to a loaded position.
Figure 8:
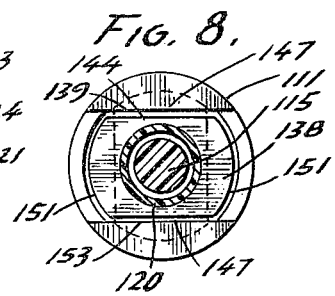
FIG. 8 is a view in vertical section taken along line 8—8 of FIG. 7.
Figure 9:
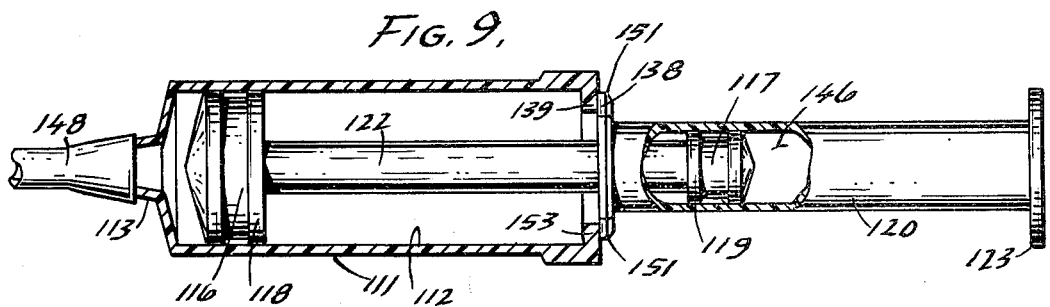
FIG. 9 is a view in vertical section showing the aspirating unit of FIG. 7 in a preloaded aspirating position.

In FIGS. 7-9, an aspirating device 110 is disclosed which also utilizes the same basic double-headed piston member 115 with oppositely disposed sealing elements 118 and 119 in reciprocating relation to barrel member 111 having a nozzle 113 and opening 114. Similar numbers are indicated for similar parts as in the aspirating device 10 except that they are numbered in the 100 series. There are two distinct differences between aspirating device 110 and 10 in that the telescoping member 120 is substantially smaller in diameter in relation to barrel member 111 and does not ride against the internal wall 111 except for piston sealing element 118. Another distinct difference is that in place of a biased type clamping means 25 two oppositely disposed projecting inward wall portions 139 and 153 are provided for barrel member 111 for engagment by projecting flange 138 at the inner end of telescoping member 120.

As best seen in FIG. 8, projecting flange 138 is of a generally oval configuration with flat wall segments 144. These flat wall segments 144 are designed so that flange 138 can pass between the flat wall sections 147 of inward walls 139 and 153 yet, when flange 138 is rotated 90° in either direction and with the flange positioned to the outside of walls 139 and 153, as shown in FIG. 9, flange 138 will engage the outersurfaces of these walls by means of rounded segments 151.

OPERATION

A better understanding of the advantages of the aspirating device 10 will be had by a description of its operation. It will be appreciated that aspirating device 10 is intended to be used in aspirating fluids from the human body and primarily the uterus. The unit 10 will be assembled and packaged with a suitable covering and will have the position of the various parts as indicated in FIG. 1. In order to have sealing element 18 of piston head 16 seated against the inside of barrel member 11 and adjacent nozzle 13 it may be necessary to open the clamp valve means 49. In this position it will be noted that telescoping member 20 will also be moved in the direction of nozzle 13 so that sealing element 19 of piston head 17 will seat against closed wall member 21. When it is desired to aspirate fluid from the uterine cavity 41, clamp 49 will be closed and telescoping member 20 will be moved away from nozzle portion 13 by grasping flange 23 to ultimately assume a position for the double-headed piston member 15 as shown in FIG. 2. It will be noted that when the telescoping member was moved as previously indicated, that sealing element 19 will move away from the closed end portion 21 to thereby create a partial vacuum in the resulting compartment 46. Similarly, piston sealing element 18 will have also moved away slightly from nozzle member 13 due to the reduction of pressure in compartment 46, thereby creating a reduction in pressure in the barrel 11 between sealing element 18 and nozzle 13.

Figure 5:
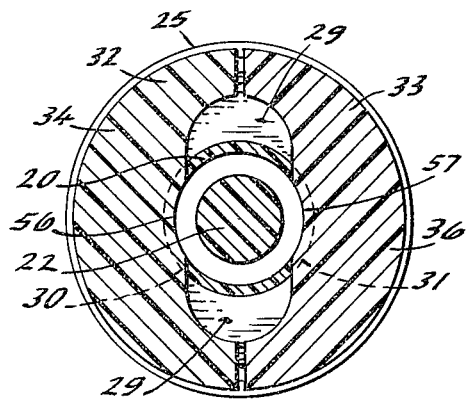
FIG. 5 is a view in vertical section taken along line 5—5 of FIG. 2 and the unit rotated 90° as in FIG. 4.

As best seen in FIG. 4, when the telescoping member 20 is in the forward position as shown in FIG. 1, the inner arcuate portions 56 and 57 of rear portions 34 and 36, respectively, will be biased against the outside of telescoping member 20. It will be noted that clamp sections 32 and 33 are spaced apart so that when the telescoping member is moved to a position as shown in FIG. 2, rear wall portions 34 and 36 will move toward each other and portions 56 and 57 enter indentations 30 and 31, as shown in broken lines in FIG. 5. It should also be noted when comparing FIG. 1 and FIG. 2 that with rear wall portions 56 and 57 engaging slots 30 and 31, respectively, that the front wall portions 35 and 37 as well as the interconnecting bridging segments 26 and 27 for clamp sections 32 and 33 will move toward barrel flange 29 and contact it. With the piston head member positioned as indicated in FIG. 2 and the previously described partial vacuums created in chamber 46 and in barrel 11 between sealing element 18 and nozzle 13, aspirating tip 42 will be positioned in the uterine cavity 41. Clamp 49 will be released as shown in FIG. 3 which, due to the reduced pressure between sealing element 18 and nozzle 13, will effect the flow of body fluid through opening 43 through tubing 48 and into barrel 11 as indicated by the numeral 45. This movement of the piston member 15 is effected by the reduction of pressure in compartment 46 and the atmospheric pressure acting on sealing element 18 to move piston 15 in the direction of arrow 55, as shown in FIG. 3, until sealing element 19 will abut against closed end wall 21 with piston head sealing element 19 providing abutment surface 24. To expel fluid 45, tubing 48 is removed from nozzle 13 or tip 42 is removed from tubing 48 and telescoping member 20 moved in the direction of nozzle 13.

It should be noted that during the aspirating effect of the previously described operation of unit 10, that once the clamp 49 is opened the movement of the piston 15 and the aspiration of fluid 45 into the barrel is automatic and without manually exerting any force on the telescoping member. The movement of the piston 15 is uniform throughout its stroke away from nozzle 13 thereby creating a uniform aspirating partial vacuum on the uterine cavity 41 and the fluid 45.

In place of the on-off clamp 49, a more precise controlled valve 52 can be utilized in the previously described manner which is shown specifically in FIG. 6.

The operation of aspirating device 110 is basically the same as that previously described for unit 10 except that the holding or biasing means is different when the aspirating unit is in the preloaded or vacuum condition a shown in FIG. 9. In order to actuate aspirating unit 10, it will be in a position as shown in FIG. 7 with sealing element 118 on piston 115 contacting barrel member 111 in the area of nozzle 113 and with sealing element 119 seating against wall 121 of telescoping member 122. A clamping element 52 or 49 will then be closed on tubing 148 and telescoping member 120 moved in a direction away from nozzle 113 until projecting flange 138 moves between inwardly extending walls 139 and 153 and to a short distance outwardly thereof. Telescoping member 120 will then be rotated 90° in either direction so that the rounded segments 151 will contact the outside of flat wall sections 147 of inward walls 139 and 153 upon release of the pulling force on flange 123. Aspirating unit 110 is then in a vacuum loaded condition as a vacuum is created in chamber 146 and between sealing element 118 and nozzle 113. It will be operated in the same manner as indicated for unit 110 upon opening of plastic tubing 148 to atmospheric or a higher pressure condition.

Aspirating units 10 and 110 are completely disposable and all of the elements with the exception of the sealing components and the tubing are composed of a resinous plastic material such as polypropylene. However, other resinous plastics could be employed such as methyl pentene polymer and if desired these elements could also be fabricated from glass.

It will thus be seen that through the present invention there is provided an aspirating device which is of the completely disposable type yet will afford a uniform vacuum throughout its operation. A vacuum is created at a constant pressure which is available by merely opening a clamp or a valve and without any pulling effect as is customary with the normal syringe. The aspirating unit is simple in its construction and can be fabricated from existing parts and materials.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:
1. An aspirating device comprising:
   a barrel member having an internal wall and defining a nozzle portion and an open end portion;
   a piston member having a first and second head portion receivable in said barrel member;
   a first sealing element carried by said first piston head portion at one end engageable with said internal wall;
   a second sealing element carried by said second piston head portion and disposed at another end;
   a hollow telescoping member having a closed end portion constructed and arranged to fit within the confines of said barrel member and in sealing engagement with said second sealing element;
   holding means operatively associated with said telescoping member and said barrel member to retain said telescoping member in a fixed position when said telescoping member is moved in a direction away from said nozzle portion; and
   means operatively associated with said nozzle portion to temporarily close said nozzle portion to the atmosphere.
2. The aspirating device as defined in claim 1 wherein said means operatively associated with said nozzle portion to temporarily close said nozzle portion is a valve member.
3. The aspirating device as defined in claim 2 wherein said valve member is a clamp member.
4. The aspirating device as defined in claim 1 further including an elongated flexible tubing with and opening and in fluid tight engagement with said nozzle portion, said elongated tubing dimensioned for entering a body cavity.
5. The aspirating device as defined in claim 1 wherein said holding means is a biased clamp member operatively carried by said barrel member to engage said telescoping member.
6. The aspirating device as defined in claim 5 wherein said biased clamp member comprises a flange on said barrel member extending in opposing directions, indentations in the telescoping member and a resiliently biased clamp portion engaging said flange and constructed and arranged to engage the indentations in the telescoping member when said telescoping member is moved outwardly from said barrel member.
7. The aspirating device as defined in claim 6 wherein said clamping portion is formed from two independent clamping sections.
8. The aspirating device as defined in claim 6 wherein said telescoping member has an external diameter slightly less than the internal diameter of said barrel to provide a close fitting relationship.
9. The aspirating device as defined in claim 8 wherein said second piston head portion has an abutment surface and said telescoping member has an end wall for contact with said abutment surface.
10. The aspirating device as defined in claim 1 wherein said holding means is a projecting flange on said telescoping member and an inwardly projecting wall portion extending from said barrel member for engagement with said projecting flange of said telescoping member.
11. The aspirating device as defined in claim 10 wherein said inwardly projecting wall portion extends from an end wall of said barrel member opposite said nozzle portion.

* * * * *